United States Patent [19]

Sung et al.

[11] 4,077,560
[45] Mar. 7, 1978

[54] DENTAL SOLDER

[75] Inventors: Pei Sung, Lawrenceville; James Lee-You, Cranbury, both of N.J.

[73] Assignee: Johnson & Johnson, New Brunswick, N.J.

[21] Appl. No.: 675,654

[22] Filed: Apr. 12, 1976

Related U.S. Application Data

[62] Division of Ser. No. 546,222, Feb. 3, 1975, abandoned.

[51] Int. Cl.² .......................... B23K 1/04; B23K 1/12
[52] U.S. Cl. .................................. 228/220; 228/263; 75/171
[58] Field of Search ..................... 228/219, 220, 263; 75/171

[56] References Cited

U.S. PATENT DOCUMENTS

| | | | |
|---|---|---|---|
| 2,714,760 | 8/1955 | Boam et al. | 75/171 |
| 2,864,696 | 12/1958 | Foreman | 75/171 |
| 2,868,639 | 1/1959 | Gonser | 75/171 |
| 2,936,229 | 5/1960 | Shepard | 75/171 |
| 3,246,981 | 4/1966 | Quass et al. | 75/171 |
| 3,727,299 | 4/1973 | Hoffmann et al. | 228/263 |

OTHER PUBLICATIONS

*Brazing Manual* American Welding Society, Inc., New York, N.Y., 2nd Edition, 1963, pp. 44–46.
*Welding and Brazing Alcoa Aluminum,* Aluminum Company of America, Pittsburgh, Pa. 1944, pp. 2–3.
Semi-Alloys, "Semi Conductor Data – Brazing and Soldering Alloys, Part II", pp. 1–4.

*Primary Examiner*—Al Lawrence Smith
*Assistant Examiner*—K. J. Ramsey

[57] ABSTRACT

The invention relates to dental solder particularly suitable for joining parts of structural frameworks made of non-precious metal alloys, the framework being used in the preparation of bridges, crowns and the like. The solder compositions consist essentially of about 69 to 75% nickel, about 14 to 19.9% chromium, about 4 to 5.5% silicon and about 2.5 to 6% boron. The compositions may be modified to include up to about 6% molybdenum to increase corrosion resistance. The solder has a fusion temperature in the range of from about 1800° to about 1950° F and a diametrial tensile strength of at least 35,000 p.s.i. and a solder joint tensile strength of at least 70,000 p.s.i.

1 Claim, No Drawings

DENTAL SOLDER

This is a division of application Ser. No. 546,222 filed Feb. 3, 1975, now abandoned.

DESCRIPTION OF THE INVENTION

This invention relates to dental restorations and particularly to dental solder to be employed in joining units of parts of metal structures employed in restorations whether or not they are subsequently faced with a tooth simulating covering.

Gold alloy has been used for many years in dental prosthesis. Because of the high cost of precious metals, numerous non-precious metal alloys have been employed for the construction of teeth, bridges, crowns and the like. Metal structures in dental constructions frequently are intricate in structure requiring casting in sections and piecing together of the sections or, may be of multiple units which need to be joined. This is normally accomplished by soldering the pieces or sections together. Whether the construction be of gold alloy or non-precious metal alloy, a gold alloy solder is most frequently used to join the sections or units of metal structures. However, the use of gold alloy solder with a non-precious alloy structure is undesirable because of the tendency of corrosion to occur at the interface as a result of galvanic conditions at the point of contact of two different metals. Conventional non-precious metal solders are not usually appropriate as dental solder since they frequently have toxic materials or may have constituents which tend to stain porcelain such as copper, cobalt and iron. Since a major use of the solder is to join structural units which are to be employed as crowns, bridges, etc, and therefore to be faced with procelain or plastic, the presence of stain producing components are highly undesirable in a dental solder. Thus, there is a need for a non-precious alloy dental solder which is free of toxic and stain-producing components while possessing appropriate fusion characteristics and adequate strength and resistance to rupture and deformation at the solder joint.

According to the present invention there has been discovered a non-precious metal alloy solder composition which is superior to existing gold alloy solders and non-precious metal alloy solders. The solder of the present invention is substantially free of toxic and stain producing materials, has a fusion range ideally suited for use with the frequently employed moderate fusing casting alloy, is adapted to be employed utilizing the existing equipment of dental laboratories, has superior physical properties, and moreover affords a solder joint of superior tensile strength. The solder of the present invention may be used in joining dental construction units made from either non-precious or precious metal alloys but when used to form joints in dental constructions of non-precious metal alloys, it has the particular advantage of being resistant to corrosion.

The dental solder alloy of the present invention comprises nickel, chromium, silicon and boron. These elements are present in the composition in proportions by weight in the following range: nickel from about 69% to 75%, chromium from about 14% to about 19.9% silicon from about 4% to about 5.5%, and boron from about 2.5% to about 6%. The solder composition may be improved particularly with respect to corrosion resistance by the inclusion of molybdenum. Thus, the foregoing composition may be modified to include molybdenum in the weight range of from 0 to about 6%. In addition to the actual amounts, the chromium to nickel ratio is critical in order to provide the required melting temperature and the properties of flowability or fluidity during the soldering process. It is desirable that the ratio be in the range of 0.18 to 0.27.

The solder composition may contain trace amounts of other metals which are normally found in the desired metals as well as minor amounts of non-metals such as carbon. However, no element other than the foregoing are deemed essential in solder compositions.

The solder alloy of the present invention has a fusion temperature in the range of from about 1800° to about 1950° F, good corrosion resistance, good oxidation resistance, tensile strength as casted of at least 35,000 p.s.i, and a Rockwell C hardness in the range of 50 to 58. As solder for non-precious metal alloys, it has tensile strength at the soldered joint of at least 70,000 p.s.i.

The solder alloy is suitable for use with non-precious metal casting alloys, especially nickel-chromium alloys. Although non-precious metal dental constructions have been employed in prosthodontics, non-precious metal dental solders have not been readily available and frequently gold alloy solders necessarily have been employed to join parts and units of dental constructions. By the present invention it is now possible to solder non-precious metal dental constructions with non-precious metal solders. This is advantageous in providing a dental construction which has superior resistance to corrosion as a result of galvanic conditions arising from the presence of different metal alloys. Moreover, the strength on the soldered joints are far superior to those soldered with gold as will be seen hereinafter.

The properties of the solder compositions of the present invention are particularly suitable for use with the frequently employed moderate fusing alloys. The fusion range of about 1800° to 1950° F is suitably below the fusion range of casting alloys which are most appropriate as structural material to be faced with dental porcelains, rendering the solder normally employable with these casting alloys without adversely affecting the alloy. Solder of the instant compositions have good flow characteristics near the 1950° F upper limit of the melting range. Thus, the solder spreads easily and quickly over clean metal surfaces, penetrates small openings and follows points of contact by capillary action. It adheres well as determined by the formation of a permanent continuous film. Moreover, the soldering may be accomplished employing the gas/oxygen or gas/air torch of the dental laboratory without the necessity of using excessive temperatures and time. Excessive temperatures may cause the parts of the dental construction to be soldered to melt while excessive temperature and time may cause gas absorption detrimental to the strength of the soldered connection.

Non-precious metal casting alloys which may be soldered with the solder composition of the present invention include nickel-chromium alloys, nickel-cobalt alloys and nickel-chromium-cobalt alloys. The composition of such casting alloys may be found in numerous standard publications such as Skinner and Phillips, "The Science of Dental Materials," W. B. Saunders Company, Philadelphia and London, 1967, and the "Dental Science Handbook" published jointly by the American Dental Association and the National Institute of Dental Research. The solder is especially useful for joining structural parts of novel nickel-chromium-silicon casting alloys which is the subject matter of application Ser. No. 376,767 filed July 5, 1973.

The tensile strengths of the soldered joints of non-precious metal alloy dental structural units soldered by the solder compositions of the present invention are far superior to the tensile strength of soldered joints of dental structural units soldered by a gold-alloy solder. Soldered joints may be produced which have more than twice the tensile strength than when soldered by gold-alloy solder. Thus, soldered joints may be prepared which have tensile strengths greater than 70,000 p.s.i. Similar soldered joints when soldered with gold-alloy solder generally have tensile strengths in the order of 35,000 p.s.i.

The solder alloy may be prepared by placing the components in a suitable vessel such as a fused alumina crucible and fusing the ingredients with appropriate mixing. While in the molten state the alloy may be poured into molds for ingot information.

The solder suitable for use in the dental laboratory may be prepared by atomizing the ingots into powder by high pressure argon or nitrogen gas and hot extruding at about 1400°–1750° F to obtain a dental solder in the form of a thin wire. The thin solder wires may also be formed by the lost wax casting technique using regular dental investment casting. The cast solder wires is generally made to be about 1/32 inch to 1/16 inch in diameter and 4 inches long and may easily be used to solder dental restorations.

The novel solder may be employed to join parts of a dental structure of cast alloy in a manner similar to that normally employed in a dental laboratory. However, by use of the solder of the present invention it is not necessary to employ fluxes. In soldering parts of a dental structure, the metal surfaces of dental restoration structural units to be joined which previously have been properly positioned either in an investment or, if a wire, in a jig or hand, are heated to the soldering temperature at the point of desired juncture in the reducing zone of the gas/oxygen or gas/air flame. The solder is then applied while the application of the flame is maintained. Upon flow of the solder the flame is removed at once and on allowing to cool a soldered joint is obtained. The soldered joint has a tensile strength far superior to a joint soldered with gold solder or presently available non-precious metal solders.

The following examples illustrate the invention but are not to be construed as limiting:

EXAMPLE I

A solder is prepared by placing in a fused alumina crucible 4.4 parts by weight of boron powder, 4.86 parts by weight of particulated silicon, 18.8 parts by weight of chromium in plate form 72.0 parts by weight of nickel shot and heating the crucible in an argon atmosphere to a temperature of about 1600° C to obtain a melt which is poured into molds for ingot information. The melt is then permitted to cool to about 500° C at which time the solid alloy is removed. The alloy thus prepared is found on analysis to be of the following composition (in percent by weight):

| | |
|---|---|
| Ni | 72.05% |
| Cr | 18.60 |
| Si | 4.69 |
| B | 3.72 |
| C | 0.03 |

(The presence of impurities such as carbon and changes such as by vaporization during fusion is reflected in analytical data).

Test rods of this alloy are cast and found to have the following mechanical properties:

| | |
|---|---|
| Diametral compression tensile strength | 41,477 p.s.i. |
| Compressive strength | 223,935 p.s.i. |
| Three point loading modulus of fracture | 113,183 p.s.i. |
| Hardness | 50.5 $R_c$ |
| percent elongation | 0.2 |
| Melting range | 1800°–1950° F |

Portions of the alloy are atomized into powder by high pressure argon gas and hot extruded at about 1400°–1750° F to obtain in a dental solder in the form of a thin wire.

The solder is employed to solder together parts of dental structures made of an alloy disclosed and claimed in aforementioned copending application. When it is used to solder one such alloy having the following composition (in percent by weight):

| | |
|---|---|
| Ni | 71.3% |
| Cr | 19.1% |
| Si | 4.1% |
| Mo | 4.1% |
| B | 1.4% | and the tensile strength of the soldered joint measured, it is found to be 73.118 p.s.i.

EXAMPLE II

Using the process of Example I, an alloy suitable for use as a solder and having on analysis the following composition in percent by weight is prepared:

| | |
|---|---|
| Ni | 71.4% |
| Cr | 14.2% |
| Si | 4.4% |
| B | 5.2% |
| Mo | 4.8% |
| C | 0.03% |

The alloy is used to solder dental structure of a composition similar to that described in Example I.

EXAMPLE III

In a manner similar to that described in Example I, solders of Compositions A, B and C are prepared and their physical properties determined. The compositions and physical properties are set forth in Table I. The amounts of the elements employed is designated in the table as "Original Composition" and the composition of the alloy as determined by analysis is designated "Final Alloy Composition."

TABLE I

| | A | | B | | C | |
|---|---|---|---|---|---|---|
| Chemical Composition | Original Composition | Final Alloy Composition | Original Composition | Final Alloy Composition | Original Composition | Final Alloy Composition |
| Ni | 74.8% | 75.09% | 73.4% | 74.07% | 75.0% | 71.04% |
| Cr | 15.6% | 14.09% | 17.2% | 15.68% | 15.7% | 18.47% |

TABLE I-continued

| Chemical Composition | A Original Composition | A Final Alloy Composition | B Original Composition | B Final Alloy Composition | C Original Composition | C Final Alloy Composition |
|---|---|---|---|---|---|---|
| B | 4.3% | 4.06% | 4.2% | 3.59% | 4.3% | 6.0% |
| Si | 5.2% | 5.14% | 5.2% | 5.09% | 4.8% | 4.34% |
| C | — | 0.07% | — | 0.04% | — | 0.03% |
| Diametrical Tensile Strength (p.s.i.) | 42,000 | | 47,680 | | 36,860 | |
| Compressive Strength (p.s.i.) | — | | 185,000 | | — | |
| Three Point Loading Modulus of Factor (p.s.i.) | 102,000 | | 124,550 | | 93,540 | |
| Hardness ($R_c$) | 52 | | 57.8 | | 54.8 | |
| Melting Point (° F) | 1800–1950° | | 1800–1950° | | 1800–1950° | |

All solders show excellent solderability. When a solder of Composition A is employed to join structural units made of the alloy described in Example I and the tensile strength of the soldered joint determined, it is found to be 87,000 p.s.i.

We claim:

1. A method for joining units of a dental restoration comprising:

heating the metal surfaces of the dental restoration structural units to be joined at the point of desired juncture in the reducing zone of a flame;

introducing to the heated metal surfaces, a dental solder formed from an alloy consisting of, on a weight percent basis, from about 65% to 75% nickel, about 14 to 19.9% chromium about 4 to 5.5% silicon, about 2.5 to 6% boron and 0 to about 6% molybdenum;

maintaining the flame until the flow of solder has initiated; and thereafter, removing the unfused solder and the heat source and allowing to cool to obtain a soldered joint having a tensile strength of at least 70,000 p.s.i.

* * * * *

UNITED STATES PATENT AND TRADEMARK OFFICE
CERTIFICATE OF CORRECTION

PATENT NO. : 4,077,560
DATED : March 7, 1978
INVENTOR(S) : Pei Sung and James Lee-You It is certified that error appears in the above-identified patent and that said Letters Patent are hereby corrected as shown below:

At Column 4, Line 23, delete "in."
At Column 4, Line 38, "73.118" should be -- 73,118 --.

Signed and Sealed this

Tenth Day of October 1978

[SEAL]

Attest:

RUTH C. MASON
*Attesting Officer*

DONALD W. BANNER
*Commissioner of Patents and Trademarks*